(12) United States Patent
Holland

(10) Patent No.: US 11,484,665 B2
(45) Date of Patent: Nov. 1, 2022

(54) SAFETY SYRINGE

(71) Applicant: OWEN MUMFORD LTD, Oxfordshire (GB)

(72) Inventor: Damian Alexander Holland, Oxfordshire (GB)

(73) Assignee: Owen Mumford Limited, Oxfordshire (GB)

( * ) Notice: Subject to any disclaimer, the term of this patent is extended or adjusted under 35 U.S.C. 154(b) by 662 days.

(21) Appl. No.: 16/071,114

(22) PCT Filed: Jan. 19, 2017

(86) PCT No.: PCT/GB2017/050114
§ 371 (c)(1),
(2) Date: Jul. 19, 2018

(87) PCT Pub. No.: WO2017/125732
PCT Pub. Date: Jul. 27, 2017

(65) Prior Publication Data
US 2020/0324057 A1   Oct. 15, 2020

(30) Foreign Application Priority Data
Jan. 19, 2016 (GB) ..................... 1600982

(51) Int. Cl.
*A61M 5/32* (2006.01)
*A61M 5/315* (2006.01)

(52) U.S. Cl.
CPC ........ *A61M 5/3245* (2013.01); *A61M 5/3243* (2013.01); *A61M 5/3257* (2013.01);
(Continued)

(58) Field of Classification Search
CPC .......... A61M 5/31511; A61M 5/31578; A61M 5/31583; A61M 5/321; A61M 5/3243;
(Continued)

(56) References Cited

U.S. PATENT DOCUMENTS

| | | | |
|---|---|---|---|
| 5,201,720 A | * | 4/1993 | Borgia .................. A61M 5/326 604/198 |
| 5,562,626 A | | 10/1996 | Sanpietro |

(Continued)

FOREIGN PATENT DOCUMENTS

| | | |
|---|---|---|
| CN | 200957235 Y | 10/2007 |
| CN | 101909679 Y | 11/2013 |

(Continued)

OTHER PUBLICATIONS

International Search Report, dated May 18, 2017, from corresponding PCT/GB2017/050114 application.

(Continued)

*Primary Examiner* — Shefali D Patel
(74) *Attorney, Agent, or Firm* — Quarles & Brady LLP

(57) ABSTRACT

An apparatus for use with a syringe for providing a safety syringe, the safety syringe including a plunger configured during an inward stroke to expel a substance from a hypodermic needle attached at an open end of a barrel of the syringe, the apparatus including: a biasing member configured to bias a sheath towards a closed position at least partially covering the hypodermic needle, wherein the biasing member is configured to be released at a point on the inward stroke of the plunger to urge the sheath towards the closed position.

16 Claims, 5 Drawing Sheets

(c)

(d)

(52) U.S. Cl.
CPC ....... *A61M 5/31581* (2013.01); *A61M 5/3213* (2013.01); *A61M 5/3221* (2013.01); *A61M 5/3232* (2013.01); *A61M 2005/3254* (2013.01); *A61M 2005/3265* (2013.01)

(58) Field of Classification Search
CPC .. A61M 5/3245; A61M 5/3257; A61M 5/326; A61M 2005/3247; A61M 2005/3265; A61M 5/31501; A61M 5/31581; A61M 5/3213; A61M 5/3221; A61M 5/3232; A61M 5/3275; A61M 2005/31508; A61M 2005/3254; A61M 2205/0216
See application file for complete search history.

(56) References Cited

U.S. PATENT DOCUMENTS

| | | |
|---|---|---|
| 6,623,459 B1 | 9/2003 | Doyle |
| 2002/0156426 A1 | 10/2002 | Gagnieux et al. |
| 2005/0277894 A1 | 12/2005 | Westbye et al. |
| 2015/0133870 A1 | 5/2015 | Ashworth et al. |

FOREIGN PATENT DOCUMENTS

| | | |
|---|---|---|
| EP | 1 334 740 A1 | 8/2003 |
| EP | 2 752 211 A1 | 7/2014 |
| GB | 2 529 507 A | 2/2016 |
| WO | 2004/043524 A1 | 5/2004 |
| WO | 2009/066130 A1 | 5/2009 |
| WO | 2012/178169 A2 | 12/2012 |

OTHER PUBLICATIONS

Written Opinion, dated May 18, 2017, from corresponding PCT/GB2017/050114 application.

Office Action and Search Report, related TW Application No. 106101854, dated May 13, 2020, 12 pages. English translation included.

GB Search Report, dated Jul. 11, 2016, from corresponding GB 1600982.1 application.

* cited by examiner (a)

(b)

(c)

(d)

(a)

(b)

(c)

(d)

SAFETY SYRINGE

CROSS-REFERENCE TO RELATED APPLICATIONS

This application represents the U.S. National Stage under 35 USC 371 of International Application No. PCT/GB2017/050114, filed Jan. 19, 2017, which claims foreign priority to GB 1600982.1, filed Jan. 19, 2016, each of which is incorporated herein by reference in its entirety.

TECHNICAL FIELD

This invention relates to safety syringes and apparatus for use with syringes to convert them to safety syringes. More specifically, the invention relates to, but need not be limited to, passive safety syringes.

BACKGROUND

Broadly, syringes comprise a barrel having a hypodermic needle at one end and a plunger configured to move within the barrel such that an inward stroke of the plunger causes a substance contained within the barrel to be expelled from the needle.

Safety syringes typically include some form of safety mechanism to protect healthcare workers from the hypodermic needle after it has been injected into a patient. Exemplary safety syringes may include a sheath for covering the needle, or may cause the needle to retract within the barrel of the syringe.

SUMMARY

According to an aspect of the invention, there is provided an apparatus for use with a syringe for providing a safety syringe, the safety syringe comprising a plunger configured during an inward stroke to expel a substance from a hypodermic needle attached at an open end of a barrel of the syringe, the apparatus comprising: a biasing member configured to bias a sheath towards a closed position at least partially covering the hypodermic needle, wherein the biasing member is configured to be released at a point on the inward stroke of the plunger to urge the sheath towards the closed position.

Optionally, the biasing member is released as a result of a force applied by a user during the inward stroke of the plunger.

Optionally, the point on the inward stroke of the plunger is the end of the inward stroke of the plunger.

Optionally, the plunger is coupled to the sheath during the inward stroke and is configured to decouple from the sheath to release the biasing member.

Optionally, the apparatus further comprises a sheath retainer for retaining the sheath in an open position, holding the sheath against the biasing member in a loaded state.

Optionally, the sheath retainer comprises a lug on one of the sheath and a plunger of the syringe, the lug being configured to engage a corresponding recess on the other of the sheath and the plunger.

Optionally, the sheath is configured to contact a patient's skin and the sheath retainer is configured such that further inward movement of the plunger causes disengagement of the lug from the corresponding recess.

Optionally, the recess comprises a deflecting surface for deflecting the lug such that it disengages from the recess.

Optionally, the biasing member provides a rotational force.

Optionally, the apparatus further comprises a mechanism for translating the rotational force of the biasing member into linear motion of the sheath.

Optionally, the mechanism comprises a threaded portion coupled to the sheath for translating the rotational force of the biasing member into linear motion of the sheath.

Optionally, the plunger of the syringe is configured to rotate under the rotational force and to engage the threaded portion after decoupling of the plunger from the sheath.

Optionally, the plunger is coupled to the sheath by engagement with a keyed aperture at an opening of a barrel of the syringe such that rotation of the plunger is restricted.

Optionally, the apparatus further comprises a lock configured to retain the sheath in the closed position.

According to an aspect of the invention, there is provided a kit of parts comprising: a sheath; and a biasing member, wherein, when fitted to a syringe, the biasing member is configured to bias a sheath towards a closed position at least partially covering a hypodermic needle of the syringe, and wherein the biasing member is configured to be released at a point on the inward stroke of the plunger to urge the sheath towards the closed position.

DETAILED DESCRIPTION

Figure 1:
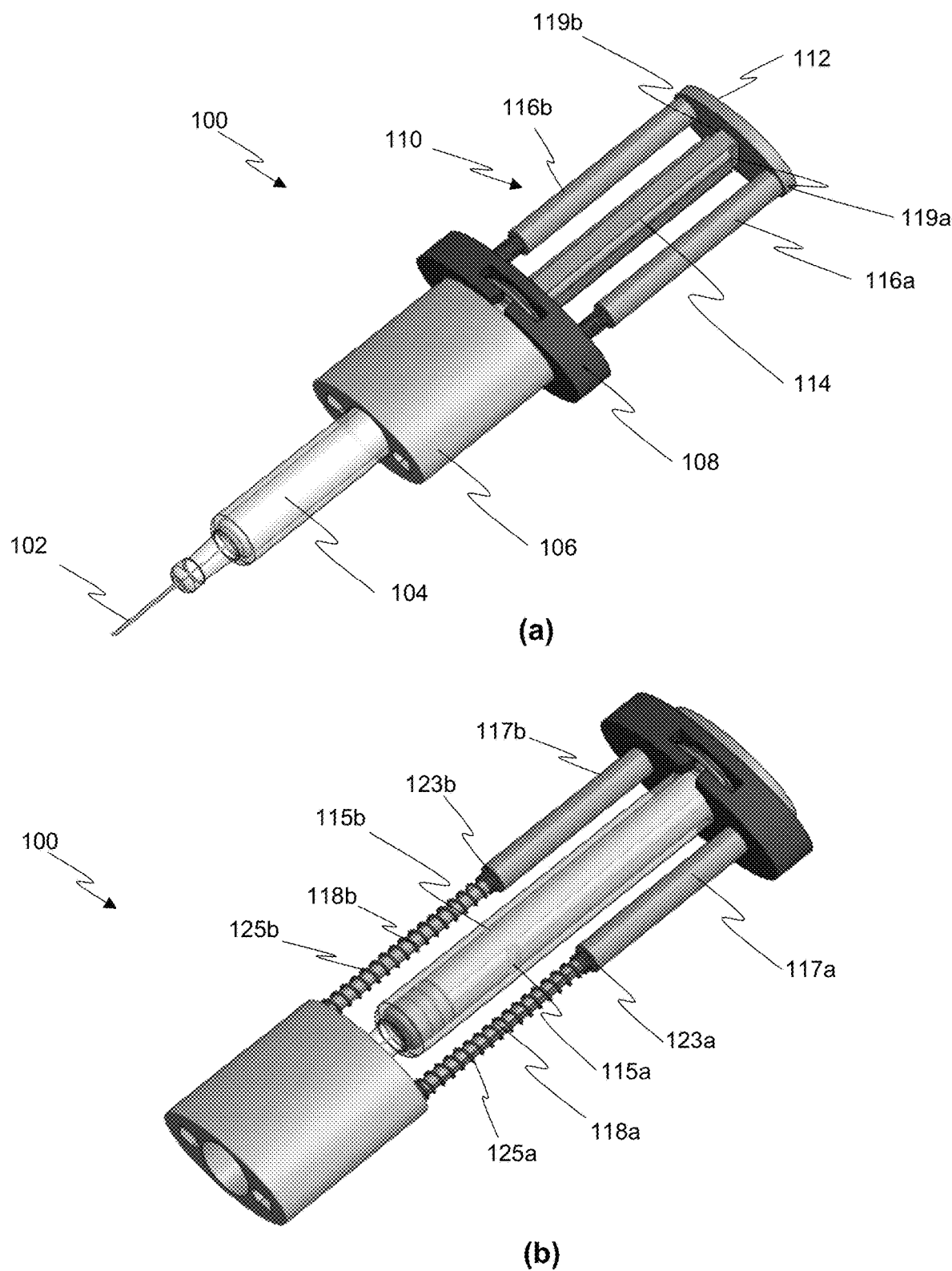
FIGS. 1a-b are isometric views of a safety syringe.

Generally disclosed herein are exemplary apparatus for use with syringes, in which a sheath is biased by a biasing member to at least partially cover a needle of the syringe. Exemplary apparatus are configured such that the biasing member is held in a loaded state during at least part of an inward stroke of a syringe until a force applied by a user releases the biasing member at a point along the inward stroke. In exemplary apparatus, the force is applied by normal operation of a plunger of the syringe. Once released, the biasing member urges the sheath over the needle of the syringe, such that the needle is at least partially covered by the sheath. In exemplary apparatus, a lock then retains the sheath in a position over the needle.

The term 'inward stroke' encompasses a stroke of the plunger longitudinal with respect to the syringe that is toward an open end of a syringe barrel, that is, in a direction to expel a substance from the barrel. The term "outward stroke" has an opposite meaning.

FIGS. 1a-b show isometric views of an exemplary apparatus fitted to a syringe for providing a safety syringe 100. The safety syringe 100 comprises a hollow needle 102 attached at the end of a barrel 104. The barrel 104 comprises an opening at the point where the needle 102 is fixed to it such that a fluid path exists between the barrel 104 and the hollow channel of the needle 102. The barrel 104 may be prefilled with a substance, for example a medicament, such that the safety syringe 100 is ready to use. The safety syringe 100 further comprises a safety syringe apparatus comprising a sheath 106, a handle 108, which is fixed in relation to the barrel 104, and a plunger 110. The plunger 110 is configured such that its inward stroke causes a substance held in the barrel 104 to be expelled from the open end of the barrel 104 and through the needle 102.

The needle 102 may be any type suitable for the task to be undertaken by the user, such as injecting a drug or other fluid into a patient or taking a fluid from a patient. In exemplary safety syringes 100, the needle 102 is fixedly attached to the open end of the barrel 104. In other exemplary safety syringes 100, the needle 102 may be removably attached to the barrel 104. In such safety syringes 100, the needle 102 may be replaced by other needles of the same or a different type.

The exemplary plunger 110 of FIG. 1 comprises a plunger head 112, a plunger shaft 114, and arms 116a and 116b.

The plunger shaft 114 is coupled to the arms 116a, 116b by the plunger head 112, and is configured to move within the barrel 104. During the inward stroke of the plunger 110, the plunger shaft 114 moves towards a needle end of the barrel 104 and during an outward stroke the plunger shaft 114 is drawn away from the needle end of the barrel 104. The exemplary plunger shaft 114 of FIG. 1 comprises a bung connector 105 (not visible in FIG. 1) for connection to a bung that travels in the barrel 104 to expel the contents of the syringe. In exemplary plunger shafts the bung connector 105 may comprise a threaded portion for securing the bung to the plunger shaft 114. In other arrangements, the bung may be connected to the plunger shaft 114 as part of the manufacturing process, or the plunger shaft 114 may butt up against the bung without any connection of the plunger shaft 114 to the bung.

Figure 2:
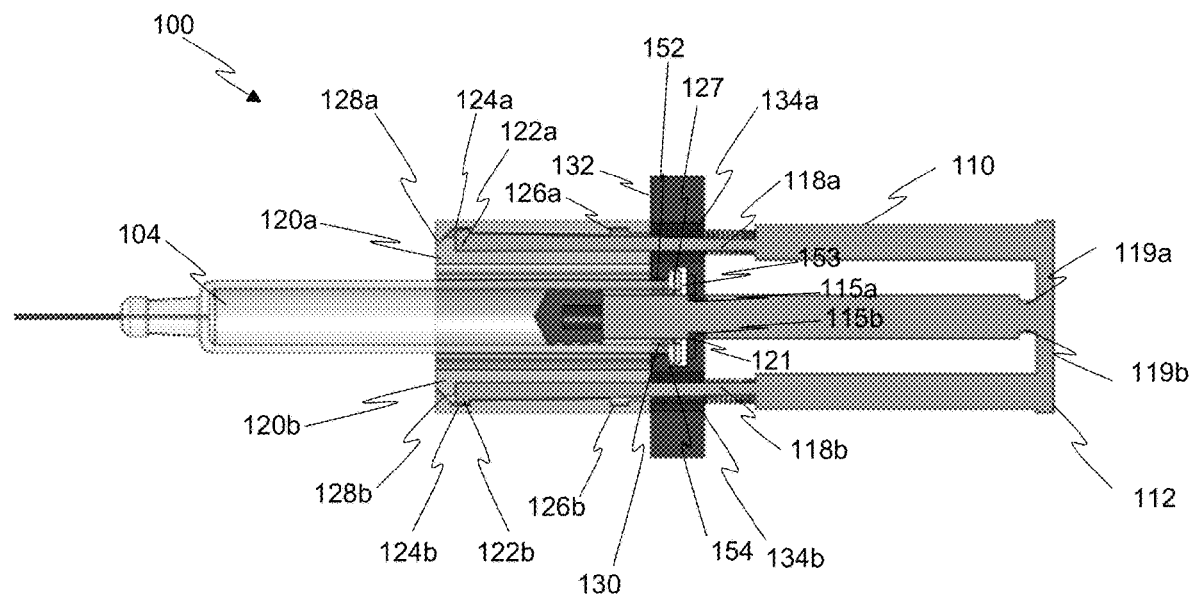
FIGS. 2a-d are section views of a safety syringe at different stages of use.
Figure 2:
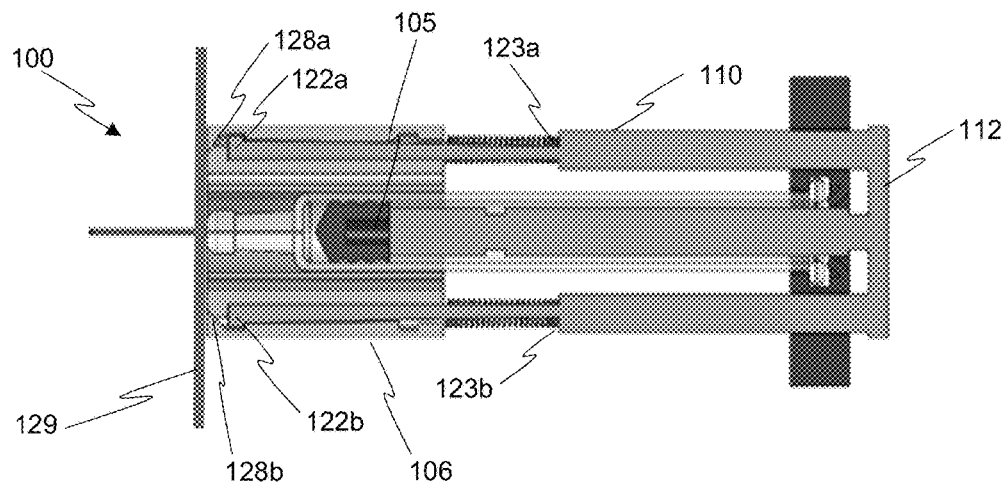
Figure 2:
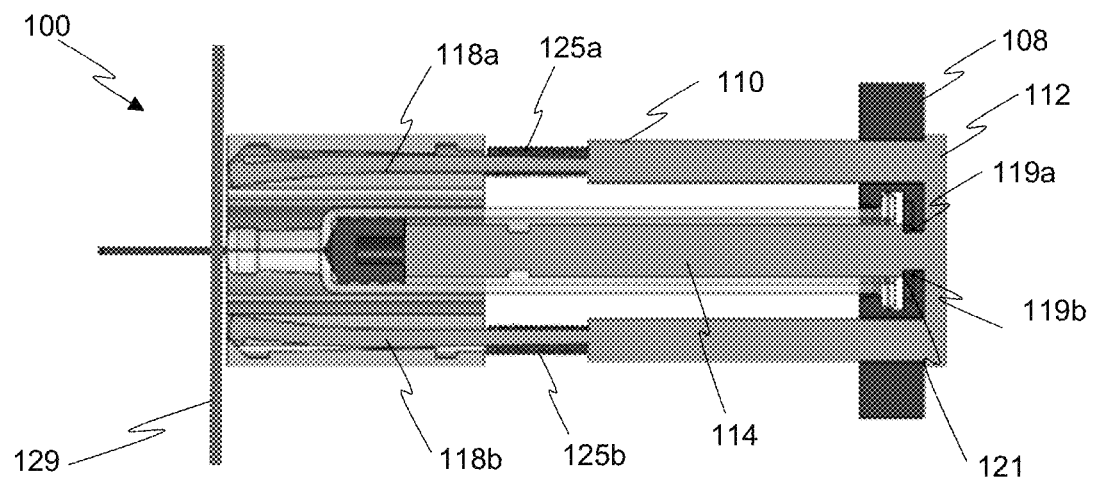
Figure 2:
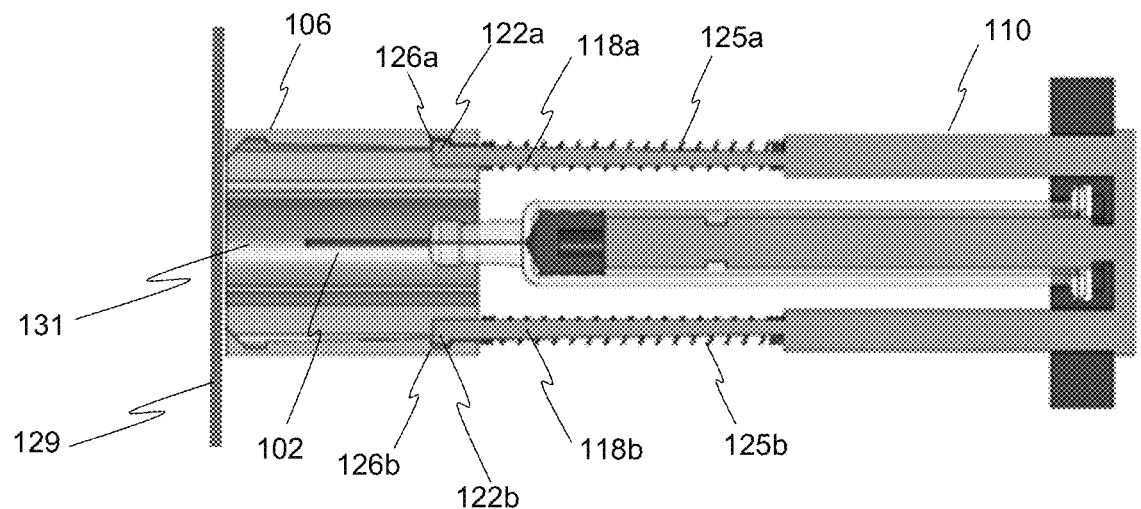

The plunger shaft 114 further comprises first plunger locking recesses 115a, 115b (visible in FIG. 1b) and second plunger locking recesses 119a, 119b (visible in FIG. 1a). The first plunger locking recesses 115a, 115b and the second plunger locking recesses 119a, 119b are configured to receive a deformable lip 121 (shown in FIG. 2a) located at an opening of the barrel 104 and, in the exemplary apparatus of FIGS. 1a-b, on the handle 108.

The arms 116a, 116b are configured to retain a biasing member in a position between a biasing surface 123a, 123b of the arms 116a, 116b and a surface of the sheath 106. In the exemplary apparatus of FIGS. 1a-b and 2a-d, the arms 116a, 116b comprise two portions, a first portion 117a, 117b and a second portion 118a, 118b. The first portions 117a, 117b are of a larger cross section than the second portions 118a, 118b, and in the exemplary plunger 110 of FIGS. 1a-b and 2a-d, the arm portions are cylindrical in shape. The first portions 117a, 117b comprise biasing surfaces 123a, 123b. The biasing members 125a, 125b, which are springs in the exemplary apparatus of FIGS. 1a-b and 2a-d, are placed over second portions 118a, 118b (e.g. around the smaller cross sectioned portions), and opposed spring ends are positioned against the biasing surfaces 123a, 123b and the sheath 106. In exemplary safety syringes, the spring may be replaced by an alternate biasing member.

Turning to FIGS. 2a-d, which show sections through the exemplary safety syringe of FIG. 1 at various stages of operation, it can be seen that the second portions 118a, 118b, of arms 116a, 116b comprise arm lugs 122a, 122b. In the exemplary plunger 110 of FIGS. 1a-b and 2a-d, the arm lugs 122a, 122b are located at the end of the second portions 118a, 118b, however these lugs might alternatively be located at other points along the second portions 118a, 118b. The arm lugs 122a, 122b are configured to be received in sheath retaining recesses 124a, 124b when the springs 125a, 125b are in a loaded state. The term "loaded state" encompasses a biasing member that is positioned such that it is capable of applying a biasing force. In the case of spring type biasing members, they may be at least partly tensioned such that a force is applied to return to a resting state. The arm lugs may be further configured to be received in sheath locking recesses 126a, 126b when the springs 125a, 125b are in a released state.

When the arm lugs 122a, 122b are engaged with the sheath retaining recesses 124a, 124b, the plunger 110 is coupled to the sheath 106. The term 'coupled' encompasses a situation in which linear movement of the plunger 110 produces linear movement of the sheath 106.

The arm lugs 122a, 122b have an angled end face to allow interaction with angled deflecting surfaces 128a, 128b. The angled deflecting surfaces 128a, 128b form at least part of a wall of the sheath retaining recesses 124a, 124b. When the arm lugs 122a, 122b are disengaged from the sheath retaining recesses 124a, 124b and the locking recesses 126a, 126b, the plunger 110 is decoupled from the sheath 106, and the sheath 106 is able to move independently of the plunger 110. It should be understood that the location of corresponding lugs and recesses could be reversed, that is, in alternate arrangements the lugs may be located on the sheath 106, with the corresponding recesses located on the arms 116a, 116b. Further, other sheath retaining means may be envisaged in other exemplary apparatus.

The handle 108 comprises a finger flange 132. Handle channels 134a, 134b run through the handle 108. The finger flange 132 may extend circumferentially around the handle 108. The finger flange 132 is configured to receive the index finger and middle finger of a user while the thumb applies a force to the plunger head 112 of the plunger 110, although any combination of fingers and/or thumb could be used. The handle channels 134a, 134b correspond to arms 116a, 116b. The handle channels 134a, 134b are configured to allow travel of arms 116a, 116b within the handle channels 134a, 134b, such that the plunger 110 may move on its stroke relative to the handle 108 and, therefore, move within the barrel 104.

The handle 108 further comprises a plunger aperture 130. The plunger aperture 130 comprises an opening 152 of substantially the same cross section as the syringe barrel 104, an elastically deformable lip 121 and a barrel retaining recess 153 comprising a ledge 154.

The barrel retaining recess is configured to receive a lip 127 of the barrel 104 and the ledge 154 is configured to retain the lip 127 of the barrel 104 within the recess 153, such that the barrel 104 is held fixed in relation to handle 108 during the inward and outward strokes of the plunger 110. The deformable lip 121 engages with the first locking recesses 115a, 115b on the plunger shaft 114 before operation of the apparatus, and with the second locking recesses 119a, 119b on the plunger shaft 114 after operation of the apparatus.

The lip 121 is configured to deform elastically when subject to a force above a threshold value, applied by the user to plunger head 112. The deformation of lip 121 disengages the lip 121 from the first locking recesses 115a, 115b, and allows movement of the plunger 110 with respect to the handle 108.

The sheath 106 comprises sheath guides, 120a, 120b. In the exemplary apparatus shown in FIGS. 1a-b and 2a-d, the sheath guides 120a, 120b are channels. The sheath guides 120a, 120b correspond to the arms 116a, 116b of the plunger 110 and are configured to allow travel of the second portion 118a, 118b, of arms 116a, 116b within the sheath channels 120a, 120b for extension of the sheath 106 over the needle 102.

The sheath 106 is operable between two positions. In a first, open position the sheath 106 is coupled to the plunger 110 and does not cover the needle 102. In a second, closed position the sheath 106 at least partially covers the needle 102 and may be locked with respect to the plunger 110. During transition between the open and closed positions, the sheath 106 is able to move independently of the plunger 110 by way of the arms 110 travelling through the sheath guides 120a, 120b.

The sheath 106 comprises a sheath retainer configured to hold the sheath 106 in the open position. The exemplary sheath retainer of FIG. 2 comprises the retaining recesses 124a, 124b. The retaining recesses 124a, 124b are engageable with the arm lugs 122a, 122b. The retaining recesses 124a, 124b comprise angled deflecting surfaces 128a, 128b. The exemplary sheath 106 of FIGS. 2a-d additionally comprises locking recesses 126a, 126b, which are also engageable with the arm lugs 122a, 122b to hold the sheath in the closed position.

In exemplary safety syringes the safety syringe apparatus may be manufactured as a plurality of separate features that can be assembled later. For example, the sheath 106 may be manufactured as one piece and the plunger 110 may be manufactured as one piece. During assembly, the two pieces may be joined together by some connection means, such as an interference or snap fit arrangement. In this way, the plunger 110 and the sheath 106 may be separate units capable of independent movement during at least part of the inward stroke of the safety syringe.

FIGS. 2a-d show sections through the safety syringe 100 at various positions along the inward stroke of the plunger 110. The operation of the safety syringe 100 will be described below with reference to FIGS. 2a-d.

FIG. 2a shows the safety syringe 100 with the plunger 110 and the sheath 106 at the outermost points of their strokes. Further, the sheath 106 is in the open position. At this point, the sheath 106 abuts the handle 108. The plunger 110 is coupled to the sheath 106, as the arm lugs 122a, 122b of the plunger 110 are engaged with the sheath retaining recesses 124a, 124b. The coupling of the plunger 110 and the sheath 106 holds the springs 125a, 125b in a compressed, loaded state, between the sheath 106 and the biasing surfaces 123a, 123b of the first portion 117a, 117b of the arms 116a, 116b. Lateral deflection of the springs 125a, 125b while in the loaded state is prevented by the second portions 118a, 118b of the arms 116a, 116b, about which the springs are positioned.

The plunger 110 is also coupled to the handle 106, as the deformable lip 121, located on the handle 106, is engaged with the first plunger locking recesses 115a, 115b on the plunger portion. The barrel 104 may be prefilled with a substance, such as a medicament.

A user may place the index finger and middle finger of one hand against the finger flange 132 of the handle portion 106 and the thumb of the same hand on the plunger head 112 of the plunger 110. The user then applies a relative force to the plunger head 112 and the handle 106 by closing the thumb towards the index and middle fingers. For the sake of clarity, this relative force will be considered herein as a force on the plunger head 112.

The force applied to the plunger head 112 elastically deforms the lip 121, which disengages the lip 121 from the first plunger locking recesses 115a, 115b. This allows the inward stroke of the plunger 110 to begin, and the plunger arms 116a, 116b begin to move through the handle channels 134a, 134b. As the plunger 110 and the sheath 106 are coupled, the inward stroke of the sheath 106 also begins and the sheath 106 moves over the barrel 104.

FIG. 2b shows the safety syringe 100 part of the way through the inward stroke of the plunger 110. The plunger 110 and the sheath 106 have moved together under the force applied to the plunger head 112 to a point at which the sheath 106 is touching the skin of a patient 129.

Once the sheath 106 contacts the skin of the patient 129, the sheath 106 is prevented from further movement. As a result, under continued application of force on the plunger head 112, the plunger 110 is able to continue its inward stroke, while the sheath 106 is held fixed. This continued movement is permitted because of the angled deflecting surfaces 128a, 128b of the sheath retaining recesses 124a, 124b. Continued application of the force on the plunger head 112 leads the arm lugs 122a, 122b to travel along the deflecting surfaces 128a, 128b and be deflected radially inwards. This in turn causes the plunger 110 to decouple from the sheath 106. The decoupling process is explained below.

The continuation of the inward stroke of the plunger 110 results in the longitudinal movement of the arm lugs 122a, 122b within the sheath retaining recesses 124a, 124b. As such, the distance between the sheath 106 and the biasing surfaces 123a, 123b of the arms 116a, 116b reduces as the plunger 110 continues its inward stroke. This serves to further compress the springs 125a, 125b.

This results in interaction between the arm lugs 122a, 122b and the angled deflecting surfaces 128a, 128b of the sheath retaining recesses 124a, 124b. The angled deflecting surfaces 128a, 128b are configured to deflect the arm lugs 122a, 122b radially inwards and so they are disengaged from the sheath retaining recesses 124a, 124b. The deflecting surfaces 128a, 128b cause inward deflection of the arm lugs 122a, 122b beyond the radial extent of the lugs such that they are no longer retained by the sheath retaining recesses 124a, 124b.

FIG. 2c shows the end of the inward stroke of the plunger 110, when all of the substance contained within the barrel 104 has been expelled. The plunger head 112 sits flush with the handle 108. The lip 121 has returned to its original shape to engage with the second plunger locking recesses 119a, 119b, located on the plunger shaft 114. This locks the plunger 110 to the handle 106. The arm lugs 122a, 122b are fully disengaged from the sheath retaining recesses 124a, 124b, with the deflection inwards of the second portion of the arms 118a, 118b with respect to the longitudinal direction.

At this point, the springs 125a, 125b are held in their compressed state by the force the user is applying to the plunger head 112, and not by the sheath retaining recesses 124a, 124b. As the user reduces the force applied to the plunger head 112 by removing the syringe needle from the patient, the springs 125a, 125b are able to extend. The extension moves the sheath 106 towards its closed position and the second portion of the arms 118a, 118b move through the sheath guides 120a, 120b as the sheath extends. As the sheath 106 is decoupled from the plunger 110, handle 108 and barrel 104, the sheath 106 extends outwards over the barrel 104 to cover the needle 102.

FIG. 2d shows the apparatus with maximum extension of the springs 125a, 125b. It should be understood that the term 'maximum extension' refers to the maximum extension allowed by the safety apparatus 100, which may be determined by the longitudinal position of the locking recesses 126a, 126b. This may or may not correspond to the maximum possible extension of the springs if they are unrestrained.

In FIG. 2d, the sheath 106 completely surrounds the needle 102 in its closed position. The end 131 of the sheath 106 extends beyond the tip of the needle 102 such that the needle is not exposed.

In the closed position, the plunger 110 is locked in relation to the sheath 106, such that the needle 102 cannot become exposed. The locking occurs once the extension of the springs 125a, 125b is such that the arm lugs 122a, 122b reach the sheath locking recesses 126a, 126b in the sheath channels 120a, 120b. At this point the arm lugs 122a, 122b engage with the sheath locking recesses 126a, 126b, and the second portion of the arms 118a, 118b return to their non-deflected state.

Figure 3:
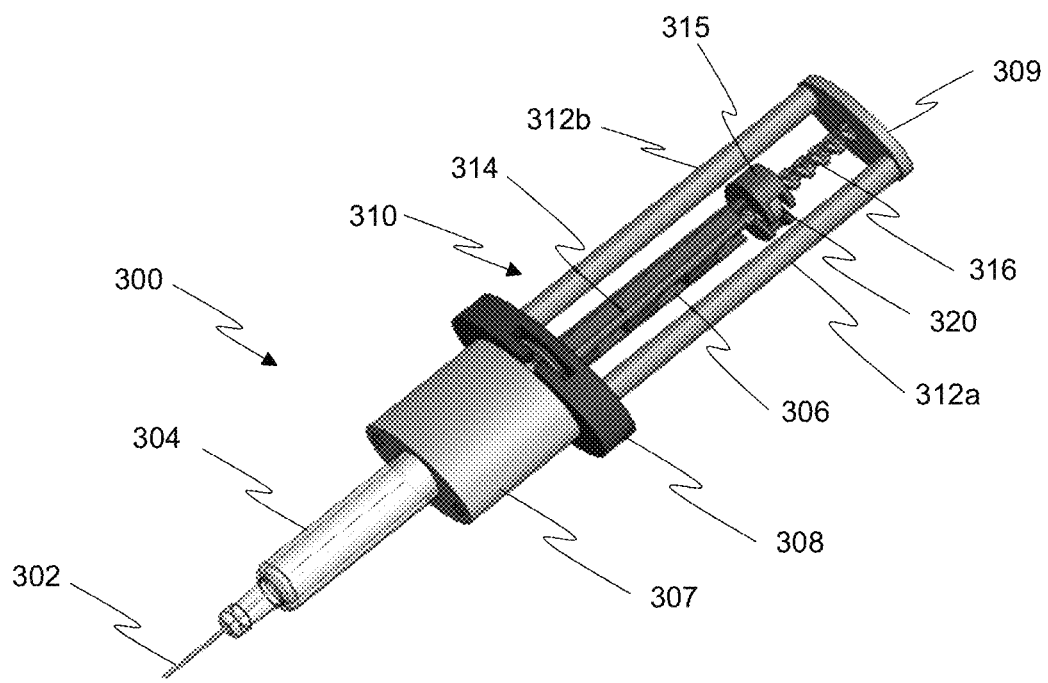
FIGS. 3a-d are isometric views of a safety syringe at different stages of use.
Figure 3:
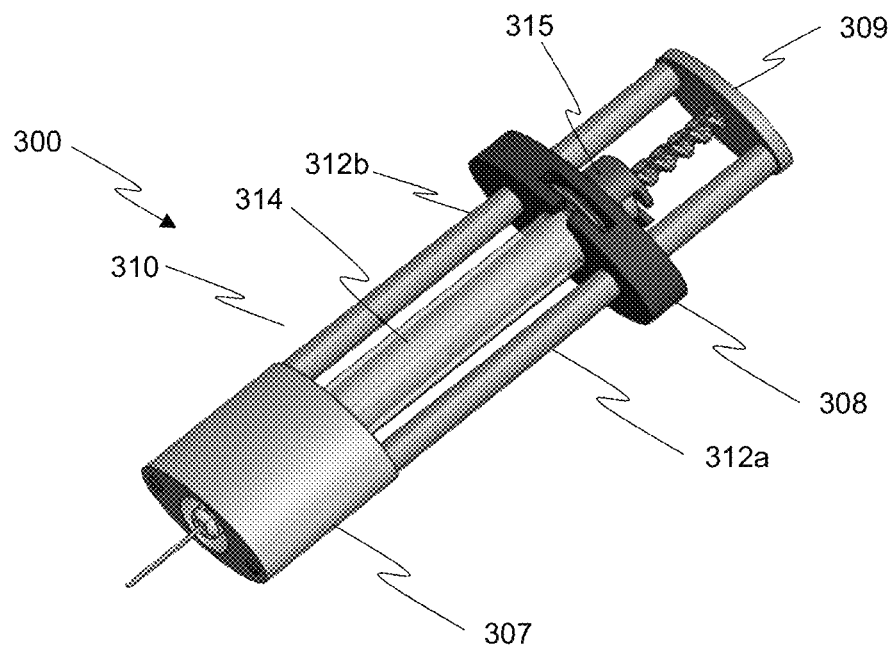
Figure 3:
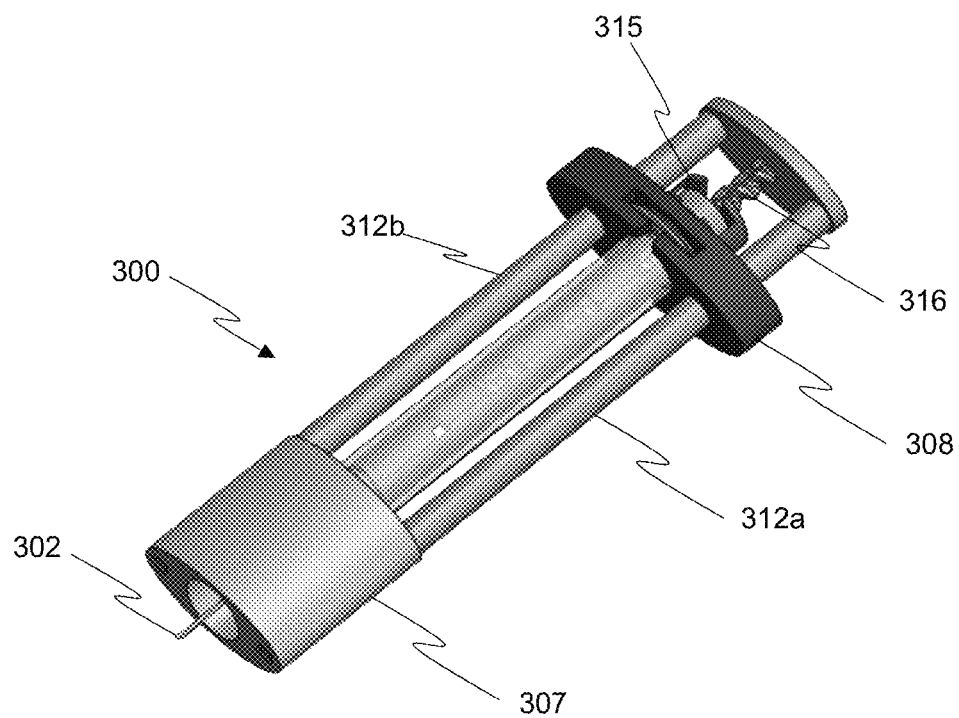
Figure 3:
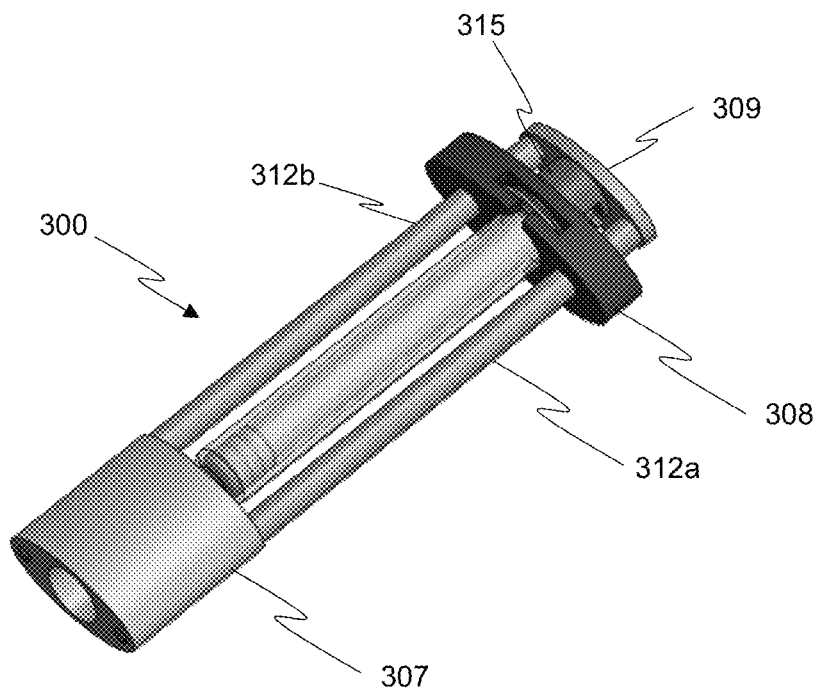

FIG. 3a shows an isometric view of an alternate apparatus fitted to a syringe to provide a safety syringe 300. The exemplary safety syringe 300 comprises a hollow needle 302 and a barrel 304 similar to those described in the embodiment of FIG. 1. The safety syringe 300 additionally comprises a plunger 306, a handle 308, and a sheath assembly 310.

The plunger 306 comprises a plunger shaft 314, and a spring housing 315. The plunger shaft 314 is configured to move in the barrel 304 in a similar way to the plunger shaft 114 of FIGS. 1a-b and 2a-d. A first portion of the plunger shaft 314 is configured to fit within an aperture in the handle 308 such that the plunger shaft 314 is unable to rotate. In exemplary apparatus, the handle aperture may be keyed and the cross section of the first portion of the plunger shaft 314 may be configured to mate with the keyed aperture. A second portion of the plunger shaft 314 is configured to rotate within the handle aperture. In this way, the plunger 306 is configured to decouple from the sheath assembly at a point on the inward stroke, as explained below.

The spring housing 315 is attached to the plunger shaft 314 and is configured to hold a biasing member in the form of a rotary spring 320. The spring housing 315 is configured to hold the rotary spring 320 in a loaded state when the plunger 306 is coupled to the sheath assembly 310, and support the rotary spring 320 in a relaxed state when the plunger 306 and the sheath assembly 310 decouple. Further, the spring housing 315 is configured to engage with the rotary spring 320, such that unfurling of the spring 320 from a loaded to an unloaded state rotates the spring housing 315 and the plunger 306.

The sheath assembly 310 comprises a sheath 307, arms 312a, 312b, a head 309 and a threaded portion, which in the exemplary apparatus of FIGS. 3a-d is a threaded rod 316. The arms 312a, 312b are cylindrical. The arms 312a, 312b are fixedly attached between the head 309 and the sheath 307. The threaded rod 316 is fixedly attached to the head 309 and located such that it is concentric with and received by the spring housing 315 and the plunger shaft 314. The spring housing 315 and/or the plunger shaft 314 are configured to engage with the threaded rod 316, such that relative rotation between the spring housing 315 and/or the plunger shaft 314 and the threaded rod 316 also cause relative linear motion therebetween. For example, the plunger shaft 314 and/or the threaded rod 316 may comprise an internal thread configured to engage the threaded rod 316. The apparatus 300 therefore comprises a mechanism for translating rotary force applied by the biasing member into linear motion of the sheath 307 and, in the exemplary apparatus of FIGS. 3a-d, the mechanism comprises the threaded rod 316 and optionally the spring housing 315 and/or the plunger shaft 314.

The handle 308 is fixed in relation to the barrel 304. The handle 308 comprises channels 318a, 318b (not visible in FIGS. 3a-d) configured to receive the arms 312a, 312b. The arms 312a, 312b are moveable within the channels 318a, 318b. As such, the sheath assembly 310 is moveable along the barrel 304, when a force is applied by a user to the head 309.

The operation of the safety syringe 300 will now be described with reference to FIGS. 3a-d.

FIG. 3a shows the safety syringe 300 with the plunger 306 and the sheath 307 at the outermost points of their strokes. The sheath 307 is in an open position. The sheath 307 abuts the handle 308, and the plunger 306 is coupled to the sheath assembly 310 by the threaded rod 316. The rotary spring 320 is held in a loaded state within the spring housing 315.

Similarly to the exemplary safety syringe 100 of FIG. 1, a user may place the index finger and middle finger of one hand against handle portion 106 and the thumb of the same hand on the head 309 of the sheath assembly 310. The user then applies a relative force to the head 309 and the handle 308 by closing the thumb towards the index and middle fingers.

The relative force applied to the head 309 allows the inward stroke of the plunger 310 to begin. The sheath assembly arms 312a, 312b begin to move through the handle channels 318a, 318b, and the sheath 307 travels further down the length of the barrel 304.

FIG. 3b shows the safety syringe 300 at a point just before the end of the inward stoke of the plunger 306. The plunger 306 and the sheath 307 have moved together under the force applied to the head 309 and the second portion of the plunger shaft 314 is about to interact with the handle aperture in the handle 308.

Continued application of the force to the head allows the second portion of the plunger shaft 314 to interact with the handle aperture such that the plunger 306 is free to rotate and is decoupled from the sheath assembly 310. As the plunger 306 is free to rotate, the rotary spring 320 is released. The rotary spring 320 unfurls, which rotates the spring housing 315 and, therefore, the plunger 306 within the barrel 304. The rotation of the plunger 306 results in an interaction between an internal thread of the spring housing 315 and/or the plunger shaft 314 and the external thread of the threaded rod 316.

As shown in FIG. 3c, the threaded rod 316 is drawn through the spring housing 315 by the rotation of the spring housing 315. This continues the inward stroke of the sheath assembly 310. The arms 312a, 312b continue to pass through the handle channels 318a, 318b, and the sheath 307 extends beyond the end of the barrel 304 to cover the needle 302 at least partially.

FIG. 3d, shows the apparatus when the inward stroke of the sheath assembly has been completed under the rotary motion of the spring 320. The rotary spring 320 has fully unfurled and the head 309 abuts the spring housing 315. The sheath 307 extends beyond the tip of the needle 302, such that the needle 302 is not exposed. In this position the sheath assembly 310 is locked in relation to the barrel 304 and the needle 302, such that the needle 302 cannot become exposed. The interaction between the external thread of the threaded rod 316 and the internal thread of the spring housing 315 and/or the plunger shaft 316 does not allow for an outward stroke of the plunger 306 by application of a force to the head 309. In order for the needle 302 to be exposed, the spring housing 315 would have to be manually rotated against the bias, which would require specific effort by the user.

The skilled person will be able to envisage other safety syringes and features thereof without departing from the scope of the appended claims.

The invention claimed is:

1. An apparatus for use with a syringe for providing a safety syringe, the apparatus comprising:
   a plunger configured during an inward stroke to expel a substance from a hypodermic needle attached at an open end of a barrel of the syringe:
   a biasing member configured to bias a sheath towards a closed position at least partially covering the hypodermic needle,
      wherein the biasing member is configured to be released at a point on the inward stroke of the plunger to urge the sheath towards the closed position, wherein the plunger is coupled to the sheath for axial movement therewith during the inward stroke and is configured to decouple from the sheath at a release point to release the biasing member,
      wherein the plunger further comprises a resiliently deformable arm configured to release the biasing member at said release point on deflection of the resiliently deformable arm by a deflection surface of the sheath.

2. The apparatus according to claim 1, wherein the biasing member is released as a result of a force applied by a user during the inward stroke of the plunger.

3. The apparatus according to claim 2, wherein the point on the inward stroke of the plunger is an end of the inward stroke of the plunger.

4. The apparatus according to claim 2, further comprising a sheath retainer for retaining the sheath in an open position, holding the sheath against the biasing member in a loaded state.

5. The apparatus according to claim 1, wherein the point on the inward stroke of the plunger is an end of the inward stroke of the plunger.

6. The apparatus according to claim 5, further comprising a sheath retainer for retaining the sheath in an open position, holding the sheath against the biasing member in a loaded state.

7. The apparatus according to claim 1, further comprising a sheath retainer for retaining the sheath in an open position, holding the sheath against the biasing member in a loaded state.

8. The apparatus according to claim 7, wherein the sheath retainer comprises a lug on one of the sheath and the plunger, the lug being configured to engage a corresponding recess on the other of the sheath and the plunger.

9. The apparatus according to claim 8, wherein the sheath is configured to contact a patient's skin and the sheath retainer is configured such that further inward movement of the plunger causes disengagement of the lug from the corresponding recess.

10. The apparatus according to claim 8, wherein the recess comprises the deflection surface for deflecting the lug such that the lug disengages from the recess.

11. The apparatus according to claim 1, wherein the biasing member provides a rotational force.

12. The apparatus according to claim 11, further comprising a mechanism for translating the rotational force of the biasing member into linear motion of the sheath.

13. The apparatus according to claim 12, wherein the mechanism comprises a threaded portion coupled to the sheath for translating the rotational force of the biasing member into the linear motion of the sheath.

14. The apparatus according to claim 12, wherein the mechanism comprises a threaded portion coupled to the sheath for translating the rotational force of the biasing member into the linear motion of the sheath, and wherein the plunger is configured to rotate under the rotational force and to engage the threaded portion after decoupling of the plunger from the sheath.

15. The apparatus according to claim 1, further comprising a lock configured to retain the sheath in the closed position.

16. A kit of parts comprising:
    a sheath;
    a biasing member; and
    a syringe comprising a plunger, the biasing member being configured to bias the sheath towards a closed position at least partially covering a hypodermic needle of the syringe,
    wherein the biasing member is configured to be released at a point on an inward stroke of the plunger to urge the sheath towards the closed position,
    wherein the plunger is coupled to the sheath for axial movement therewith during the inward stroke and is configured to decouple from the sheath at a release point to release the biasing member, and
    wherein the plunger further comprises a resiliently deformable arm configured to release the biasing member at said release point on deflection of the resiliently deformable arm by a deflection surface of the sheath.

* * * * *